United States Patent [19]

Kuhla et al.

[11] Patent Number: 4,714,707

[45] Date of Patent: Dec. 22, 1987

[54] ARYL SUBSTITUTED HETEROCYCLES FOR TREATING GASTROINTESTINAL MOTILITY DYSFUNCTION

[75] Inventors: Donald E. Kuhla, Doylestown; William L. Studt, Harleysville; Henry F. Campbell, Lansdale; John Yelnosky, Warrington, all of Pa.

[73] Assignee: Rorer Pharmaceutical Corporation, Fort Washington, Pa.

[21] Appl. No.: 570,526

[22] Filed: Jan. 13, 1984

[51] Int. Cl.[4] ............... A61K 31/095; A61K 31/39; A61K 31/42; A61K 31/425
[52] U.S. Cl. ................................. 514/361; 514/363; 514/364; 514/381; 514/384; 514/383; 514/386; 514/897; 548/125; 548/130; 548/133; 548/251; 548/263; 548/269; 548/307
[58] Field of Search ............... 514/361, 363, 364, 381, 514/384, 383, 386, 897; 548/125, 251, 130, 133, 263, 269, 307

[56] References Cited

U.S. PATENT DOCUMENTS

| | | | |
|---|---|---|---|
| 3,279,988 | 10/1966 | Buting et al. | 548/125 |
| 4,060,635 | 11/1977 | Diamond et al. | 519/596 |
| 4,147,804 | 3/1979 | Diamond et al. | 514/596 |
| 4,150,154 | 4/1979 | Diamond et al. | 514/596 |
| 4,198,409 | 4/1980 | Yelnosky et al. | 514/867 |
| 4,239,768 | 12/1980 | Rasmussen | 514/392 |
| 4,432,977 | 2/1984 | Davis | 514/513 |
| 4,440,765 | 4/1984 | Diamond et al. | 514/363 |
| 4,443,467 | 4/1984 | Ward | 514/428 |
| 4,446,142 | 5/1984 | Cohen et al. | 514/363 |
| 4,448,783 | 5/1984 | Siegel | 514/867 |
| 4,466,966 | 8/1984 | Rasmussen | 514/275 |
| 4,520,014 | 5/1985 | Newsome et al. | 514/867 |
| 4,529,723 | 7/1985 | Kuhla et al. | 514/383 |
| 4,563,475 | 1/1986 | Kuhla et al. | 514/275 |
| 4,611,011 | 9/1986 | Yelnosky et al. | 514/406 |

Primary Examiner—Morton Foelak
Assistant Examiner—Kriellion S. Morgan
Attorney, Agent, or Firm—James A. Nicholson; Alexis Barron; Martin F. Savitzky

[57] ABSTRACT

Aryl substituted diazaheterocyclic amines and their use in the treatment of gastrointestinal motility dysfunctions.

3 Claims, No Drawings

ARYL SUBSTITUTED HETEROCYCLES FOR TREATING GASTROINTESTINAL MOTILITY DYSFUNCTION

FIELD OF THE INVENTION

This invention relates to a class of pharmaceutically active compounds and to their use in the treatment of gastrointestinal disorders such as gastrointestinal motility dysfunctions and in particular the disorder known as irritable bowel syndrome (IBS).

Irritable bowel syndrome is one of the most common physical disorders observed in the practice of gastroenterology. It is typically a chronic condition characterized by abdominal pain and an alteration in bowel habits which are not due to any identifiable anatomical abnormality. Gross symptoms include either diarrhea or constipation or periods wherein patients experience both conditions. Furthermore, IBS patients frequently suffer from a heightened level of anxiety.

In recent years, investigators have characterized IBS as a primary disorder of intestinal motility, that is, a disturbance in the normal movement of intestinal contents. It patterns in the intestinal smooth muscle both in the unstimulated basal state as well as subsequent to intestinal stimulation. By way of background, the electrical activity of intestinal smooth muscle in normal patients demonstrates both a pattern of slow waves and spike potentials. The slow waves are phasic undulations in the electric potential of the smooth muscle membrane and are present throughout the intestinal tract. The spike potential activity reflects the electrical stimulus initiating smooth muscle contraction and increases following meals and stimulation.

IBS patients exhibit abnormal slow wave patterns and abnormal spike potential patterns both in the basal state and in response to meals. Additionally, IBS patients experience increases in segmental electrical activity in response to stimuli such as cholecystokinin, neostigmine, stress, and distension of portions of the intestinal tract. Segmental electrical activity is manifested by the contraction of isolated units of circular smooth muscle that constrict the bowel lumen. This constriction is non-propulsive and is believed to result in impedence to the flow of the intestinal contents. It has been suggested that increased segmental activity may result in constipation, and that decreased segmental activity may be associated with diarrhea.

A basic abnormality in the electrical pattern of IBS patients is the marked increase in the incidence of slow wave activity occuring at a frequency of 3 cycles per minute, in contrast to the predominant slow wave frequency in normal patients of 6 cycles per minute. Another striking difference between normal patients and IBS patients is reflected in the contractile activity exhibited subsequent to the ingestion of a meal. In a normal patient, colonic contractile activity will increase rapidly to 3 to 4 times its basal level for a period of about half an hour, and return to the fasting level 50 minutes later. In contrast, the contractile activity in IBS patients reaches a peak at 70-90 minutes but never reaches the maximum activity of the normal patient. As a result of this abnormal condition, the IBS patient experiences ineffective movement of the gastrointestinal contents, undue distension of the intestinal tract and heightened pain sensitivity to abdominal pressure.

The present invention relates to a method of restoring the intestinal function of an IBS patient to normal levels.

REPORTED DEVELOPMENTS

In human clinical studies, anticholinergic drugs such as clidinium bromide have been found to moderate the abnormal colonic contraction activity in IBS patients following a meal, but such therapy does not normalize the intestinal function of an IBS patient. Indeed, it has been reported that the response to anticholinergic drugs is markedly different in normal and IBS patients, and it has been suggested that the persistence of the abnormal slow wave frequency regardless of symptoms or therapy reflects the predisposition of IBS patients to respond to various stimuli in an abnormal fashion. For a recent discussion of IBS, see H. Tucker and M. M. Schuster, *Irritable Bowel Syndrome: Newer Pathophysiologic Concepts,* "Advances in Internal Medicine," Vol. 27, pp. 183-204 (1982), hereby incorporated by reference.

Other drugs suggested for use in IBS treatment include diphenoxylate. When diarrhea is present, diphenoxylate in combination with stool softeners has been suggested as a treatment. However, diphenoxylate possesses morphine-like properties and therefore, its use may result in gastrointestinal spasms, respiratory depression and narcotic dependence.

Mild sedation with phenobarbitol or tranquilizers such as Librax ® has also been suggested for the treatment of IBS.

In U.S. Pat. No. 4,239,768, N-aryl-N'-(2-imidazolidinylidine) urea compounds are disclosed as being useful in the treatment of IBS. There is no disclosure in the '768 that the imidazolidinylidene compounds have been found useful in human clinical studies.

SUMMARY OF THE INVENTION

This invention relates to a class of compounds defined by Formula I

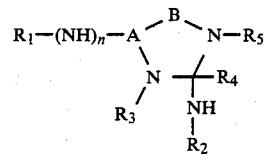

wherein:
A is nitrogen or carbon;
B is oxygen, sulfur, $NR_6$ or $C=X$;
X is oxygen or sulfur;
n is 0 or 1, provided that n is 0 when A is nitrogen;
$R_1$, $R_2$ and $R_6$ are each independently phenyl, substituted phenyl, hydrogen, alkyl or aralkyl;
$R_3$ and $R_4$ form a double bond and $R_5$ is hydrogen or alkyl when A is nitrogen;
$R_4$ and $R_5$ form a double bond and $R_3$ forms a double bond with A when A is carbon;
provided that at least one of $R_1$ and $R_2$ is other than hydrogen and alkyl;
and, the pharmaceutically acceptable salts thereof.

This invention relates to a method for treating a patient suffering from a motility dysfunction of the gastrointestinal tract, including, for example, a patient suffering from IBS, comprising medicating said patient with a therapeutic amount of a compound of Formula I.

DETAILED DESCRIPTION

Compounds of this invention which are preferred include those where:

either $R_1$ or $R_2$ is substituted phenyl of the formula

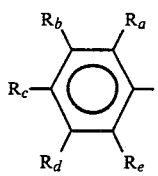

wherein $R_a$, $R_b$, $R_c$, $R_d$ and $R_e$ are each independently hydrogen, halo, alkyl, haloalkyl, nitro, amino, alkylamino, hydroxy, aralkoxy or alkoxy.

The more preferred compounds of the present invention include those where:

A is carbon and B is oxygen or sulfur;
A is carbon and B is C=O or C=S; and
A is nitrogen and B is C=O or C=S.

Also preferred are compounds wherein at least one of $R_a$ and $R_e$ is other than hydrogen and preferably either halo or alkyl.

A special embodiment of this invention comprises the compounds which have:

$R_a$-loweralkyl substitution;
$R_a$, $R_e$-diloweralkyl substitution;
$R_a$, $R_e$-loweralkyl, alkoxy substitution;
$R_a$, $R_e$-loweralkyl, halo substitution;
$R_a$, $R_e$-alkyl, nitro substitution;
$R_a$, $R_c$, $R_e$-triloweralkyl substitution, or
$R_a$, $R_c$, $R_e$-loweralkyl, dihalo substitution.

A further special embodiment of this invention comprises compounds and the use thereof which have:

$R_2$ hydrogen or loweralkyl substitution.

It is well known in the pharmacological arts that non-toxic acid addition salts of pharmacologically active amine compounds do not differ in activities from their free base. The salts provide a water soluble form of the compounds.

The amines of this invention may be readily converted to their non-toxic acid addition salts by customary methods in the art. The non-toxic salts of this invention are those salts the acid component of which is pharmacologically acceptable in the intended dosages. Such salts include those prepared from inorganic acids, organic acids, higher fatty acids, high molecular weight acids. Examples of such acids are:

| | |
|---|---|
| hydrochloric acid, | succinic acid, |
| hydrobromic acid, | glycolic acid, |
| sulfuric acid, | lactic acid, |
| nitric acid, | salicylic acid, |
| phosphoric acid, | benzoic acid, |
| methane sulfonic acid, | nicotinic acid, |
| benzene sulfonic acid, | phthalic acid, |
| acetic acid, | stearic acid, |
| propionic acid, | oleic acid, |
| malic acid, | abietic acid. |

"Alkyl" means an aliphatic saturated hydrocarbon of one to about ten carbon atoms.

"Loweralkyl" means an alkyl hydrocarbon group from one to about five carbon atoms.

"Loweralkoxy" means an alkoxy group containing from one to about five carbon atoms.

"Substituted phenyl" means a phenyl group having one or more phenyl hydrogen atoms substituted by alkyl, halo, haloalkyl, nitro, amino, alkylamino, dialkylamino, hydroxy, aralkyloxy or alkoxy.

The preferred "aralkyl" groups are benzyl and phenethyl.

The preferred "aralkoxy" group is benzyloxy.

The preferred "haloloweralkyl" group is trifluoromethyl.

Compounds of Formula I may be prepared from the corresponding substituted anilines which are either commercially available or prepared by standard methods known in the art. Examples of appropriate anilines are disclosed in U.S. Pat. Nos. 3,914,306 and 3,976,643 hereby incorporated by reference. The following reaction sequences are exemplary of the preparations available to one skilled in the art.

The method of Ramuz and Tilley, Helv. Chim. Acta. 63(4), 832–840 (1980) is used to prepare the 1,2,4-oxadiazole compounds by way of an N-cyano intermediate which upon treatment with an hydroxylamine results in the desired compound (Scheme I).

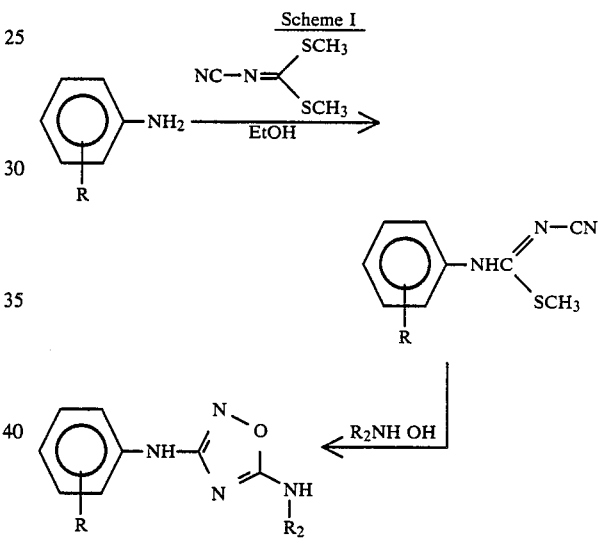

The sulfur analogs (1,2,4-thiadizoles) may be prepared by means of the oxidative base catalyzed cyclization of the corresponding amidinothioureas, which are described in U.S. Pat. No. 4,418,208, hereby incorporated by reference, and which may be prepared from the corresponding phenylguanidine and isothiocyanate. (See Scheme II)

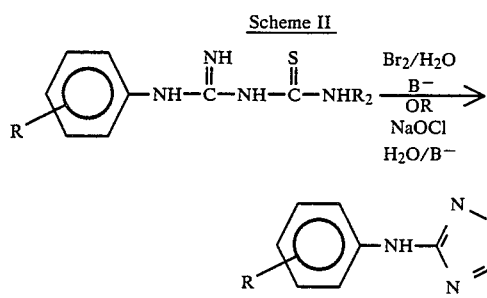

The preparation of compounds wherein $R_2$ is phenyl or substituted phenyl is depicted in Scheme III below. The appropriate aniline may be transformed into a isothiocyanate in the customary manner, such as the transformation of the benzoyl chloride, reacted with cyanamide in the presence of strong base such as KOH, and subsequently cyclized with chloramine in aqueous base. See, Walek and Pallas, *Tetrahedron*, 32, 623–7 (1976).

Scheme III

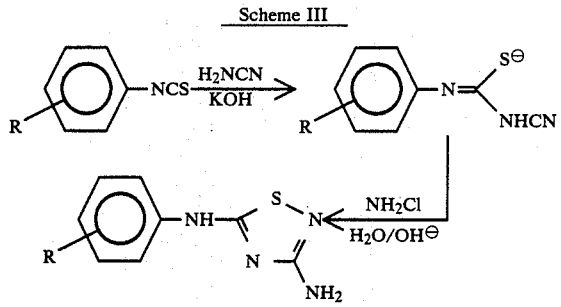

The oxygen analog may be prepared by means of oxidative cyclization of the amidinourea (Scheme IV) Prepared in accordance with procedures known in the art, such as U.S. Pat. Nos. 4,060,635, 4,117,165, 4,147,804, 4,150,154 and 4,203,920, hereby incorporated by reference.

Scheme IV

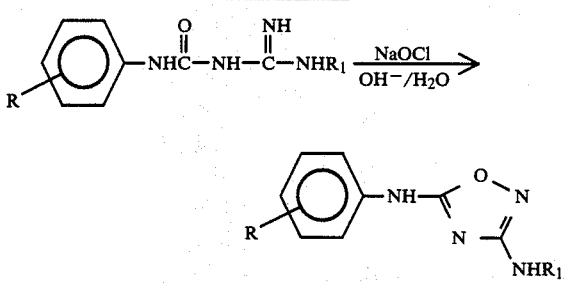

Compounds of Formula I wherein A is a carbonyl or thiocarbonyl group may be prepared by the condensation cyclization product of a glyoxylate ester and $R_2$-substituted guanidine. Treatment of the cyclization product with $P_2S_5$ transforms the carbonyl functionality to the thiocarbonyl.

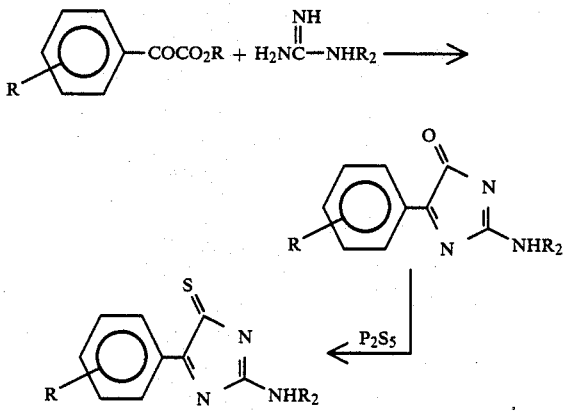

The glyoxylate ester and guanidine starting material are either commercially available or may be prepared by standard preparations.

The following is a detailed example showing the preparation of a compound according to the present invention.

The Preparation of 2-Amino-4-(2-methylphenyl)-5-imidazolone

Sodium (11.5 g, 0.5 g.atoms) is dissolved in 250 ml of absolute ethanol under nitrogen and the clear solution cooled to 0° C. A solution of guanidine hydrochloride (47.8 g, 0.05 moles) in 100 ml of absolute ethanol is added dropwise and the resultant mixture stirred at 0° C. for one hour. The reaction mixture is filtered under a blanket of nitrogen to remove sodium chloride. The stirred clear filtrate is treated at 0° C. with a solution of ethyl 2-methyl phenyl glyoxylate (76.9 g, 0.4 moles) in 100 ml of absolute ethanol. The mixture is allowed to warm to room temperature over a period of about two hours and the ethanol removed in vacuo. The residue is partitioned between methylene chloride and saturated aqueous sodium bicarbonate. The organic layer is dried and evaporated to give after recrystallization 2-amino-4-(2-methyl phenyl)-5-imidazolone.

During the course of human clinical studies, it has been found that the condition of many IBS patients improves significantly when these patients are administered a pharmaceutical composition including a compound which exhibits positive activity in the pharmacological test procedures described below.

Charcoal Motility

This procedure measures the effect of test compounds on normal intestinal motility.

A charcoal suspension (10 ml/kg of a 10% suspension of activated charcoal, U.S.P. in 0.5% methylcellulose) is given orally to groups of laboratory mice 30 minutes after an oral dose of the test compound or vehicle. The mice are sacrificed 30 min after receiving the charcoal and the intestines are carefully removed without stretching and placed lengthwise on moist paper. The length of intestine (pyloric sphincter to caecum) and the distance traveled by the charcoal as a fraction of that length are evaluated for each animal and group means are compared and expressed as percentage inhibition.

Castor Oil Induced Diarrhea

Castor oil diarrhea is the result of both altered motility and increased intestinal secretions. This procedure measures the effectiveness of test compounds on abnormal motility and hypersecretory intestinal states. Male Swiss-Webster mice (25–30 g) or female Wistar rats (180–210 g) are dosed orally with a test compound or vehicle 1 h before receiving a standard dose of castor oil orally (0.3 ml in mice, 1.0 ml in rats). The animals are individually caged and examined for the presence of diarrhea hourly for 6 h after castor oil challenge. Diarrhea is defined as the presence in the stools of fluid material which stained the absorbent paper placed beneath the cage. Control animals had 100% incidence of diarrhea at 3 h in mice and 4 h in rats. For tolerance studies both male and female Wistar rats (140–160 g) are given the test compound at doses of 2, 10 and 50 mg/kg once daily for 14 consecutive days. Five rats (fasted overnight) per dose per sex and appropriate controls are challenged with castor oil on days 1, 2, 7 and 14 of the experiment. On the test days, test compound or vehicle is given as usual and 1 h later the animals are challenged with castor oil and observed for diarrhea as described above.

Isolated Guinea Pig Ileum Test

Sections of the terminal ileum of guinea pigs, 2–3 cm long, are suspended in a 50-ml bath of Tyrode solution (37° C., pH 7.5) at 0.5 g tension and oxygenated with 95% $O_2$-5% $CO_2$. Isometric contractions are recorded with a Grass force displacement transducer and a Beckman dynograph with a strain-gauge coupler. Isotonic contractions are recorded with a Harvard isotonic smooth muscle transducer and a Beckman dynograph. A concentrated spasmogen solution of histamine, cholecystokinin, $BaCl_2$, serotonin, dimethyl phenyl piperizinium chloride, $PEG_2$ or acetylcholine is added to the bath. Both cumulative and single doses of spasmogens are used. The concentration of test compound necessary to halve the spasmogenic response ($ID_{50}$) is determined at levels of the test compound that gave approximately 75% of the maximum response ($ED_{75}$).

It is believed that IBS effective compound described above also exhibits a positive response in connection with the following test procedures.

Charcoal Motility—Abnormal Motility Induced by Neostigmine and Quinidine

The test procedure is described in the following references, hereby incorporated by reference:
Schuster, *Gastrointestinal Disease*, p. 880 (1983); and
Garrett et al, *Gut*, 7:562 (1966).

Isolated Rabbit Duodenum Test

This assay measures the direct spasmolytic effect of test compound on intestinal circular smooth muscle. Segments of rabbit duodenum, 2–3 cm long, are suspended in a 50-ml bath of Ringer's solution (37° C., pH 7.3) at 0.5 g tension and oxygenated with 95% $O_2$-5% $CO_2$. A concentrated spasmogen solution of morphine, cholecystokinin, $PEG_2$ or acetylcholine is added to the bath in cumulative and single doses. The maximum response to each drug is taken as 100% and all lesser responses are calculated as a percentage of the maximum response. Contractions are recorded with a Grass force displacement transducer and a Beckman dynograph with a strain-gage coupler. The concentration of test compound necessary to halve the spasmogenic response ($ID_{50}$) is determined at levels of the test compound that give approximately 75% of the maximum response ($ED_{75}$).

Intestinal Motility in Anesthetized Dogs

This procedure measures the effect of the test compounds on intestinal circular and longitudinal smooth muscle contractions both in the basal state and stimulated state. Treatment of the subject animal with spasmogens such as cholecystokinin and $PEG_2$ produces modified motility patterns useful for studying the motility normalizing effect of the test compounds. Female beagle dogs are inplanted under aseptic conditions with 8 extraluminal contractile force strain-gauge transducers Prior to recording intestinal contractile activity, the dogs are anesthetized with sodium pentobarbitol (35 mg/kg i.v.). Contractile activity is monitored from the circular axis of the proximal and mid-duodenum, two sites on the terminal ileum and the proximal and mid-colon. The ileal sites are also monitored for longitudinal contractile activity. Contractions are recorded on a Beckman Dynograph. The response of intestinal motility in both fed and fasted states to several doses of the test compound is recorded. For recording of fasted intestinal activity, the dogs are not fed (water ad libitum) for 18 h prior to the start of recording; fed animals are given 450 g of canned dog food immediately before the experiment.

It is also believed that a further indication of IBS effectiveness is local anesthetic activity.

The compounds of Formula I above have a useful degree of effectiveness in treating a patient suffering from irritable bowel syndrome or other gastrointestinal motility dysfunctions. These compounds may be administered to the patient either orally or parenterally. The preferred route of administration is by oral means in the form of tablets, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such corositions may contain one or more agents selected from the group consisting of sweetening agents, flavoring agents, coloring agents and preserving agents, in order to provide a pharmaceutically elegant and palatable preparation. Tablets which contain the active ingredient in admixture with non-toxic pharmaceutically acceptable excipients are suitable for the manufacture of tablets. These excipients may be the following: inert diluents, for example, calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to delay disintegration and absorption.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions may be formulated using the following excipients: suspending agents, for example, sodium carboxymethyl-cellulose, methyl-cellulose, hydroxypropylmethylcellulose, sodium alginate, polyvinylpyrrolidine, gum tragacanth and gum acacia; dispersing or wetting agents such as a naturally occurring phosphatide, for example, lecithin; condensation products of an alkylene oxide with fatty acids, for example, polyoxyethylene stearate; condensation products of ethylene oxide with long-chain aliphatic alcohols, for example, heptadecaethyleneoxy-cetanol; condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan mono-oleate. The said aqueous suspensions may also contain one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The pharmaceutical compositions useful in the present invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents.

The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active compound may be administered alone or in admixture with other agents having the same or different pharmacological properties.

Further, these compounds may be tableted or otherwise formulated for oral use so that for every 100 parts by weight of the composition, there are present between about 5 and about 95 parts by weight of the active ingredient. The dosage unit form will generally contain between about 0.1 mg and about 50 mg of the active ingredients of this invention. The preferred unit dose is between about 0.5 mg and about 10 mg. The compositions may be taken 1-8 times daily depending on the dosage unit required.

The dosage regimen in carrying out the methods of this invention is that which insures maximum therapeutic response until improvement is obtained and thereafter the minimum effective level which gives relief. Thus, in general, the dosages are those that are therapeutically effective in the treatment of irritable bowel syndrome. In general, the oral daily dose can be between about 0.01 mg/kg and about 1 mg/kg (preferably in the range of 0.05-0.50 mg/kg/day), bearing in mind, of course, that in selecting the appropriate dosage in any specific case, consideration must be given to the patient's weight, general health, age, and other factors which may influence response to the drug.

Parenteral administration may be carried out using comparative dosages taken from the oral compositions. In general, the parenteral dosage will be less than the oral dose and normally within the range of about ½ to about 1/10 the oral dose but, of course, this will depend or the absorption characteristics of the compound employed. Dosages would be in the customary manner; however, in general, parenteral administration may be carried out neat or the compound may be utilized with a sterile vehicle as mentioned above. Dosage unit forms of about 0.1 to about 50 mg, and preferably about 1 to about 10 mg are useful. A recommended daily parenteral dose is about 0.002 to about 0.2 mg/Kg/day, preferably about 0.01 to about 0.1 mg/Kg/day.

The way in which IBS affects individuals can vary from one individual to another. For example, there are patients who have the condition for years, indeed most, if not all, of their lives. As noted above, IBS is believed to be a dysfunction in intestinal motility resulting in a range of distressing symptoms which increase or decrease in severity as a result of any number of factors, including stress. Some IBS patients may appear relatively free of the syndrome for days, weeks or even months, but experience acute episodes at any given time. On the other hand, other patients may suffer a higher and relatively constant incidence of symptoms such as abdominal pain and alternating periods of diarrhea and constipation.

The present invention provides an IBS patient with a choice of therapy. Since some normalizing effect is usually experienced relatively quickly, for example, within an hour to within about a day or two after the start of medication pursuant to the invention, the patient may be medicated for short periods of time, for example, on a daily basis for about a day to about two weeks to avoid acute occurences of IBS symptoms at times of stress or at times when other aggravating factors are present. Such acute therapy may be discontinued when aggravating factors abate, and resumed when the patient feels that continued therapy would be beneficial. For those patients experiencing a remission of the underlying motility dysfunction, therapy may be discontinued. On the other hand, patients who are constantly being troubled by the discomfort of IBS symptoms may require continuous or maintenance therapy which involves medication on an essentially continuing daily basis. Observations of various patients have revealed that, soon after the discontinuance of therapy, IBS symptoms reappear. For such patients, medication on a maintenance basis appears to be in order.

We claim:

1. A method of treating a patient suffering from a gastrointestinal motility dysfunction comprising medicating said patient with an effective gastrointestinal motility normalizing amount of a compound according to the formula

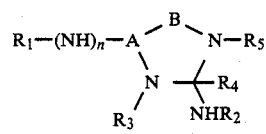

wherein:
  A is nitrogen or carbon;
  B is oxygen, sulfur, NR$_6$ of C=X;
  X is oxygen or sulfur;
  n is 0 or 1, provided that n is 0 when A is nitrogen;
  R$_1$, R$_2$ and R$_6$ are each independently phenyl, substituted phenyl, hydrogen, alkyl or aralkyl;

$R_3$ and $R_4$ form a double bond and $R_5$ is hydrogen or alkyl when A is nitrogen;

$R_4$ and $R_5$ form a double bond and $R_3$ forms a double bond with A when A is carbon;

provided that at least one of $R_1$ and $R_2$ is other than hydrogen and alkyl; and wherein:

substituted phenyl means phenyl substituted by one or more of halo, alkyl, haloalkyl, nitro, amino, alkylamino, hydroxy, aralkoxy or alkoxy;

or, a pharmaceutically acceptable acid addition salt thereof.

2. A method according to claim 1 wherein said gastrointestinal motility dysfunction is irritable bowel syndrome.

3. A method according to claim 1 wherein said patient is medicated with an oral daily dose of about 0.01 mg to about 1 mg of said compound per kg of body weight or with a daily parenteral dose of about 0.002 mg to about 0.2 mg of said compound per kg of body weight.

* * * * *